United States Patent [19]

Miyata et al.

[11] 4,223,984
[45] Sep. 23, 1980

[54] COLLAGEN SOFT CONTACT LENS

[75] Inventors: Teruo Miyata, Tokyo, Japan; Albert L. Rubin, Englewood, N.J.; Michael W. Dunn, New Rochelle, N.Y.; Kurt H. Stenzel, Englewood, N.J.

[73] Assignee: Opticol Corporation, Stamford, Conn.

[21] Appl. No.: 26,945

[22] Filed: Apr. 4, 1979

Related U.S. Application Data

[63] Continuation of Ser. No. 753,556, Dec. 22, 1976, abandoned.

[51] Int. Cl.² .............................................. G02C 7/04
[52] U.S. Cl. ........................ 351/160 H; 128/DIG. 8; 260/123.7; 264/202
[58] Field of Search ...................... 351/160 R, 160 H; 260/123.7; 264/202; 128/DIG. 8

[56] References Cited

U.S. PATENT DOCUMENTS

| | | | |
|---|---|---|---|
| 2,920,000 | 1/1960 | Hochstadt | 260/123.7 X |
| 3,443,261 | 5/1969 | Battista et al. | 351/160 X |
| 3,530,037 | 9/1970 | Nishihara | 351/160 X |
| 3,738,913 | 6/1973 | Johnson | 260/123.7 X |
| 3,760,045 | 9/1973 | Thiele et al. | 351/160 X |
| 3,955,012 | 5/1976 | Okamura et al. | 351/160 X |

FOREIGN PATENT DOCUMENTS 39174 10/1974 Japan ........................................ 351/160

OTHER PUBLICATIONS

Tanner, J. C. et al., "Lamellar Keratoplasty: Use of a Collagen Graft for Corneal Replacement," *Eye, Ear, Nose, & Throat Monthly*, Aug. 1968, pp. 268-372.

Fettes, E. M., *Chemical Reactions of Polymars*, 1964, pp. 380-387.

*Primary Examiner*—John K. Corbin
*Assistant Examiner*—Scott J. Sugarman
*Attorney, Agent, or Firm*—Edward J. Mahler

[57] ABSTRACT

Soft contact lenses are made from solubilized, defatted, transparent, cross-linked collagen, and/or chemically-modified collagen.

18 Claims, No Drawings

COLLAGEN SOFT CONTACT LENS

This is a continuation of application Ser. No. 753,556 filed Dec. 22, 1976, now abandoned.

This invention relates to a soft contact lens consisting of colagen and/or chemical modifications of such collagen. The invention also relates to the production of such lenses preferably by irradiation of the collagen substance in a lens mold with gamma rays.

Contact lenses have been known as a commercial product for over 25 years. Contact lenses to date have been made from chemically synthesized materials which do not occur in nature. For example, most early contact lenses were made from polymethylmethacrylate or chemical modifications thereof, from hydroxyethylmethacrylate, from cellulose acetate butyrate, from silicones, etc. To the knowledge of the applicants no lens, prior to this invention, was made from naturally occurring animal materials and especially from materials having physiological and immunological properties possessed by constituents of the eye itself, e.g., the cornea. The state of the art on contact lenses is reviewed in a current article "A Contact Lens Update"--Contact Lens Forum, p. 16-23 (May 1976).

The chemistry, molecular structure and biochemical properties of collagen have been well established. An up-to-date review article by the current inventors (Annual Review of Biophysics and Bioengineering, Vol. 3, p. 231-253, 1974) contains an excellent compilation of references on the subject.

Collagen is a major protein of connective tissue such as skin, cornea, etc., and can be solubilized, separated and purified by the treatment with proteolytic enzymes (other than collagenase), e.g., proctase, pepsin, trypsin and pronase. Enzyme solubilized collagen is telopeptides-poor, relatively inexpensive, and useful as a biomedical material. The collagen is redispersed as a clear aqueous gel up to 30% (the balance being essentially water) and placed in a lens mold (glass, brass, stainless steel, and/or plastic) and gamma-irradiated to polymerize the collagen. A collagen soft contact lens prepared by this method is optically clear, flexible, stable and comfortable to wear.

Collagen has been used by the present inventors in various drug and medical applications, e.g., as a vehicle for drug delivery in opthalmic application; as dialysis membranes; as vitreous implants, and in other medical and surgical applications. Their studies have been published widely in medical journals. The inventors know of no utilizations of collagen described hereunder as a soft contact lens material prior to their own discovery.

The present invention is illustrated in detail in the following description: Calfskin collagen was used as a starting material, but other sources such as steer hide, cowhide and pigskin may also be utilized. Dehaired and cleaned skin is solubilized with a protelytic enzyme (pepsin for example) and solubilized collagen is precipitated at pH 7 after inactivation of enzyme activity by caustic treatment at pH 10. Precipitated solublized collagen is defatted by repeated extractions with ethanol-ethyl ether mixture (1:1). This defatting process is essential to obtain transparent collagen gel for lens production.

Solubilized collagen contains many $NH_2$ and COOH groups in its structure, and chemical modifications of the molecule can be readily made, e.g., all or some of the amino groups may be acylated by reaction with a mixture of acetic anhydride and acetic acid, or other anhydride such as succinic anhydride. All or some of the carboxyl groups contained in the molecule may be esterified by the standard reaction with acidified alcohol, preferable a water soluble aliphatic alcohol, such as methanol, ethanol, etc. In the above reactions the isoelectric point of collagen can be controlled, either negative or positive, or completely neutralized. Excellent soft contact lenses have been made from succinylated and methylated collagen.

Gels having collagen concentrations ranging from 1% to 30% can be utilized for lens production, but the preferable concentration is 1% to 20% with the balance being water. As the collagen content of the gel increases substantially above about 20%, the material becomes gummy and difficult to handle and work. A collagen soft contact lens of higher water content is more pliable, superior in oxygen diffusion and more comfortable to wear. However, the mechanical strength of the lens is improved with decreasing water content.

Cross-linking of the solubilized transparent collagen is necessary in order to stabilize the molecule. Cross-linking is accomplished by irradiation with gamma or ultraviolet rays or by heating, drying or simple aging. Cross-linking can also be accomplished by treating with certain chemicals such as aldehyde, e.g., formaldahyde, glutaraldahyde or with acids such as chromic acid. The mechanism of cross-linking of collagen is well-known and has been fairly well documented. In the preparation of soft contact lenses in accordance with this invention, the preferred cross-linking method is irradiation in the presence of nitrogen. Nitrogen atmosphere is preferred to air because the presence of nitrogen increases the cross-linking of collagen while maintaining the rate of breakdown of collagen at a low level. Irradiation is preferred to chemical treatment since the irradiation process introduces no potentially toxic foreign material into the collagen gel structure.

The effectiveness of gamma-irradiation is a function of the collagen concentration of the gel and of the atmosphere of the irradiation. For example, the gamma-irradiation in presence of air induces some damage of the collagen molecule concurrent with introduction of cross-linkages. The irradiation in the presence of nitrogen mimimizes the destruction of collagen and enhances gel stabilization by cross-linking. The optimal irradiation dose depends on the collagen concentration. Irradiation of 500~900 K rads at a dose rate of 82 K rads per hour is necessary to introduce enough cross-linkages into 5% collagen gel; however, a dose of 1200~1600 K rads is required for 10% collagen gel in presence of nitrogen.

Chemically modified collagens can be also used as a lens material as well as native collagen (without chemical modification). Since native collagen is soluble in acidic pH, clear gel is obtained only below about pH 4.0. Lens material made from this gel must be neutralized. On the other hand, chemically modified collagen such as succinylated collagen, or methylated collagen is soluble in physiologic condition (pH 6-8); and neutralization of the lens material is not necessary. The effect of gamma-irradiation is similar on native and chemically modified collagens.

Glass, stainless steel, brass and plastics (teflon, polyethylene, polycarbonate) may be used as a lens mold material. Glass and metals are generally preferably to plastics because of the stability against gammairradiation.

The present invention may be further understood from the following examples:

EXAMPLE 1

Fresh calfskin (about 5 kg.) was dehaired, cleaned by shaving and cut into small pieces. The skin was solubilized in 10 liters of water (pH 2.5, HCl) by addition of 1 g of pepsin (approximate ratio of enzyme to collagen is 1/400) and kept at 20° C. for five days with intermittent stirring. The resulting viscous solubilized collagen was filtered through cheesecloth, its pH adjusted to 10 by NaOH and allowed to stand for 24 hours at 4° C. to inactive the pepsin. The pH of collagen was then adjusted to 7 to 8 (HCl) and collagen precipitate was collected by centrifuging. Fatty constituents were then removed from the collagen. To one part of collected collagen was added two parts of fat solvent, e.g., ethanol-ethyl ether mixture (1:1) and the mixture was homogenized in a Waring blender. Collagen was separated from solvent by squeezing in cheesecloth and homogenized again with the same volume of solvent. After being squeezed it was air-dried to remove solvent and redissolved in acidified water (pH about 3.0) to make collagen gel.

On the lower concave part of a lower lens mold (glass) was placed 0.2 g of 5% clear collagen gel and centrifuged for 30 minutes at 3000 rpm at 10° C. to make the collagen gel spread evenly across the mold surface. After 10 minutes evacuation in vacuum, the upper convex part of the lens was pushed onto the lower mold containing the collagen gel and the entire mold transferred to an irradiation vessel. The vessel was flushed and filled with nitrogen and gamma-irradiated for 10 hours at a dose rate of 82 K rads per hour. The molded collagen lens was neutralized by phosphate-saline buffer, (pH 7.2) and transferred to normal saline. The lens was placed on the convex part of a teflon mold, frozen and trephined while the lens was frozen. The finished lens was kept in normal saline solution. This lens is optically clear, flexible and stable, and displays excellent properties as a soft contact lens.

The irradiation was carried out in a Gammator M type gamma irradiator obtained from Radiation Machinery Corporation, Parsippany, New Jersey and such irradiation equipment is not part of the inventive subject matter hereunder. The glass vessel containing the lens mold during irradiation was a standard, relatively wide-mouth, two-hole rubber-stopped vessel permitting removal of air and filling with nitrogen.

the lens molds (which likewise do not form part of this invention), were manufactured from brass, glass and plastic. The mold consists of a lower concave part and an upper convex part. The surface of the convex part, when the mold is closed, reaches the surface of the concave section, except for the desired thickness of the collagen lens. The desired thickness is approximately 0.4 millimeters, preferrably about 0.3 millimeters. Most lens material was finished with a trephine (cylindrical instrument with one razor-sharp circular cutting end), to a tapered edge lens. Instead of trephining, however, a lathe operation may also be used to finish the lens material.

EXAMPLE 2

A soft lens was prepared by a procedure similar to Example 1 except 12% collagen gel, a stainless steel mold and irradiation time of 20 hours were substituted. Again the resulting lens was optically clear, flexible and stable, and displayed excellent properties as a soft contact lens.

EXAMPLE 3

Stabilized, defatted collagen prepared in Example 1 was succinylated by the following procedure: Five grams of collagen were solubilized in 2 liters of acidified water (pH 3.0, Hcl) and the pH thereafter adjusted to 9.0 by NaOH solution. Acetone solution (100 ml) containing 2 g succinic anhydride was gradually added to the collagen suspension. During the addition of succinic anhydride the pH of collagen suspension was maintained at about 9.0 by NaOH solution. Succinylated collagen was precipitated by acidification to about pH 4.2, washed repeatedly with water and freeze-dried. Transparent 2.5% succinylated collagen gel of pH 7 was placed on the lower mold part (brass) indicated and processed in the same way as Example 1 except that 8 hours irradiation was employed. The resulting lens was completely transparent, pliable, and sufficiently strong to function as a soft contact lens. It is very comfortable to wear.

All of the lenses prepared above are susceptible of modification to prescription values by known optical techniques. Thus, soft contact collagen lenses can be prepared for use by patients requiring known normal sight corrective measures, e.g., incorporation of spherical power.

The advantages of soft lens made from solubilized collagen from a medical standpoint are summarized as follows:

1. Successful implantation of a material into the corneal stroma requires that the material be inert and highly permeable to water, nutrients, oxygen and carbon dioxide. To date collagen is the only material used for contact lenses that can be so implanted without subsequent rejection. All other materials used for contact lenses are extruded when implanted in the cornea.

2. The collagen/water ratio of the cornea and the collagen contact lens are strikingly similar. These two materials are closely related structurally, physiologically and immunologically. All other contact lens materials are totally unrelated to the collagen protein of the cornea.

The advantages from the consumer of wearer standpoint are summarized as follows:

1. The gas and water vapor permeability of the collagen membrane make it ideally suited for a constant wear contact lens without disrupting essential metabolic pressures in the cornea.

2. The similarity of this protein and the principal protein of the cornea make allergic and toxic reactions between the two very unlikely.

3. The low cost of preparation of the collagen lens material indicates a low cost to the consumer.

4. Collagen contact lenses are soft, pliable and transparent. Spherical power can be incorporated into them.

Having described the invention in the above detail, what is claimed is:

1. As an article of manufacture a soft contact lens consisting of a lens-shaped, subsequently cross-linked gel of solubilized, defatted, collagen, said gel comprising 1.0 to 30.0 wt. % collagen and the balance water.

2. A soft contact lens of claim 1 in which the lens-shaped collagen gel is chemically cross-linked.

3. As an article of manufacture a soft contact lens consisting of a lens-shaped, subsequently cross-linked gel of enzyme-solubilized, telopeptide-poor, defatted collagen, said gel comprising 1.0 to 30.0 wt. % collagen and the balance water.

4. A soft contact lens of claim 3 in which the collagen gel content is 1 to 20 wt. %.

5. A soft contact lens of claim 3 in which the collagen gel content is 5 to 12 wt. %.

6. A soft contact lens of claim 3 in which the collagen is chemically-modified collagen.

7. A soft contact lens of claim 6 in which the collagen is esterified collagen.

8. A soft contact lens of claim 7 in which the collagen is methylated collagen.

9. A soft contact lens of claim 6 in which the collagen is acylated collagen.

10. A soft contact lens of claim 9 in which the collagen is succinylated collagen.

11. A method for the manufacture of a soft contact lens which comprises solubilizing collagen from a source thereof to produce a collagen extract, removing fatty constituents from the extract, converting the extracted and defatted collagen to form a transparent gel having a collagen concentration of 1–30 wt. % forming said contact lens of such gel and cross-linking the lens.

12. A method according to claim 11 in which the lens-shaped gel is chemically cross-linked.

13. A method for the manufacture of a soft contact lens which comprises treating a source of collagen with a proteolytic enzyme to produce an extract of telopeptide-poor collagen, removing fatty constituents from the extract, converting the extracted, defatted collagen to form a transparent gel having a collagen concentration of 1 to 30 wt. %, forming said contact lens of such gel, and cross-linking the lens.

14. A process according to claim 13 in which the cross-linking is carried out by irradiation with gamma rays in the presence of nitrogen.

15. The process of claim 13 in which the collagen concentration of the gel is in the range of 1% to 30% with the balance being water.

16. The process of claim 13 in which the transparent gel is formed into a lens in a lens mold.

17. A process according to claim 13 in which the collagen is succinylated prior to shaping and cross-linking.

18. A process according to claim 13 in which the collagen is methylated prior to shaping and cross-linking.

* * * * *